United States Patent [19]

Trubiano et al.

[11] Patent Number: 4,551,177

[45] Date of Patent: Nov. 5, 1985

[54] COMPRESSIBLE STARCHES AS BINDERS FOR TABLETS OR CAPSULES

[75] Inventors: Paolo C. Trubiano; James J. Kasica, both of Somerville, N.J.

[73] Assignee: National Starch and Chemical Corporation, Bridgewater, N.J.

[21] Appl. No.: 603,021

[22] Filed: Apr. 23, 1984

[51] Int. Cl.$^4$ .......................... C08B 31/00; C08L 3/00
[52] U.S. Cl. .................................. 106/210; 106/213; 127/32; 127/71; 536/102
[58] Field of Search .................... 127/32, 71; 106/210, 106/213; 536/102

[56] References Cited

U.S. PATENT DOCUMENTS

| | | | |
|---|---|---|---|
| 1,677,615 | 7/1928 | Boidin | 127/32 |
| 2,056,104 | 9/1936 | Hueter | 127/32 |
| 2,070,576 | 2/1937 | Bochskadl | 127/32 |
| 2,178,235 | 10/1939 | Lauterbach | 127/32 |
| 2,373,016 | 4/1945 | Daly et al. | 127/70 |
| 3,034,911 | 5/1962 | McKee et al. | 106/210 |
| 3,355,307 | 11/1967 | Schoenberger | 106/213 |
| 3,453,368 | 7/1969 | Magid | 424/250 |
| 3,490,742 | 1/1970 | Nichols et al. | 252/99 |
| 3,622,677 | 11/1971 | Short et al. | 424/361 |
| 4,072,535 | 2/1978 | Short et al. | 106/210 |
| 4,369,308 | 1/1983 | Trubiano | 536/106 |
| 4,383,111 | 5/1983 | Takeo et al. | 536/102 |
| 4,384,005 | 5/1983 | McSweeney | 426/250 |

Primary Examiner—Theodore Morris
Attorney, Agent, or Firm—Margaret B. Kelley; Edwin M. Szala

[57] ABSTRACT

A compressible starch, useful as a binder for tablets prepared by direct compression or dry granulation or as a binder-diluent for capsules, is prepared by treating a cold-water-insoluble, granular starch (e.g., corn or waxy corn starch) with an acid, and/or alpha-amylase enzyme at a temperature below the starch's gelatinization temperature. The treated starch is characterized by altered, weakened granules with a less dense interior and disrupted surface. The compressible starch when admixed with a wet granulation binder (e.g., pregelatinized starch) is useful as a binder for tablets prepared by wet granulation as well as direct compression or dry granulation or as a binder-diluent for capsules.

20 Claims, 13 Drawing Figures

UNMODIFIED WAXY CORN

COMPRESSIBLE STARCHES AS TABLET BINDERS
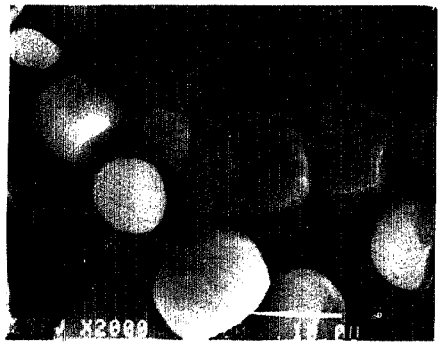
Fig.1 UNMODIFIED WAXY CORN
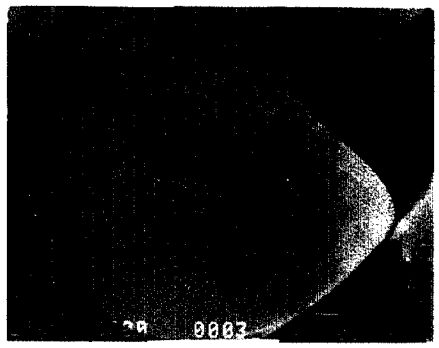
Fig.2 UNMODIFIED WAXY CORN
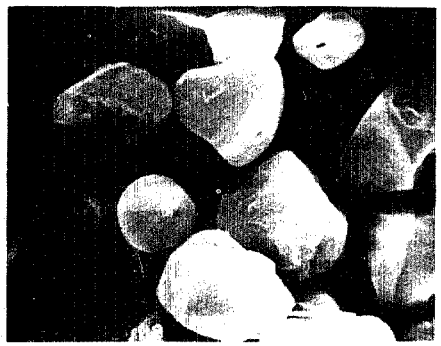
Fig.3 ACID-TREATED WAXY CORN
Fig.4 ACID-TREATED WAXY CORN

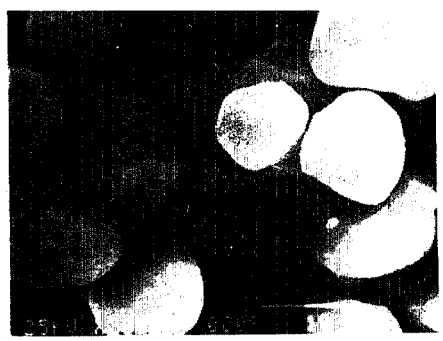
Fig.5 ENZYME-TREATED WAXY CORN (Mild Treatment)
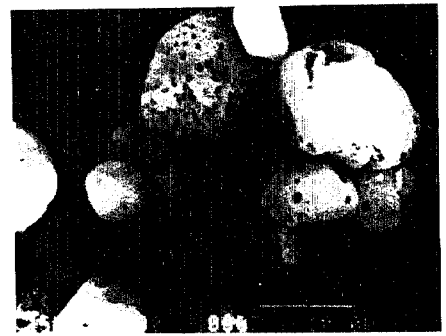
Fig.6 ENZYME-TREATED WAXY CORN (Strong Treatment)
Fig.7 ACID/ENZYME-TREATED WAXY CORN

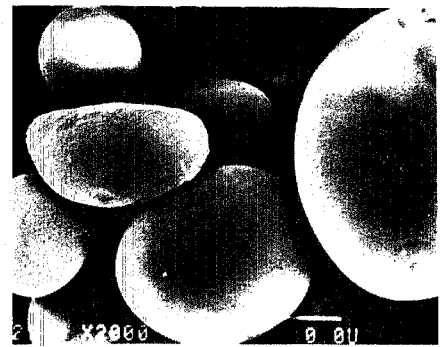
Fig.8 UNMODIFIED POTATO
Fig.9 ACID/ENZYME-TREATED POTATO
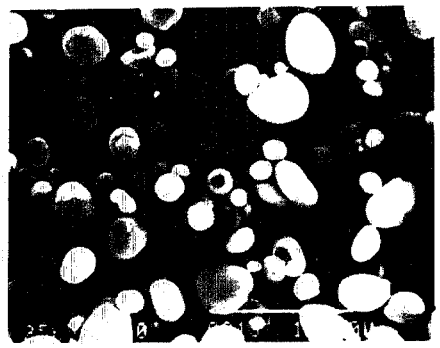
Fig.10 ACID/ENZYME-TREATED POTATO
Fig.11 ACID/ENZYME-TREATED POTATO

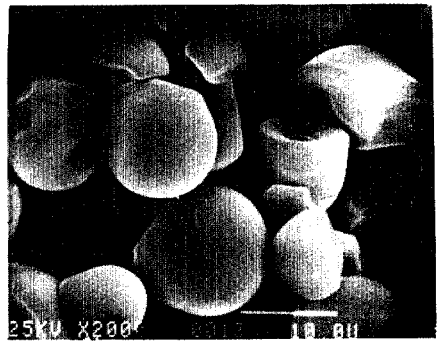
Fig.12 UNMODIFIED TAPIOCA
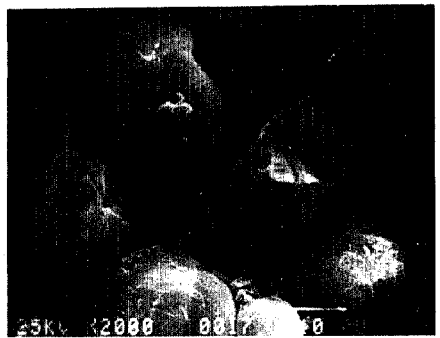
Fig.13 ACID-TREATED TAPIOCA

COMPRESSIBLE STARCHES AS BINDERS FOR TABLETS OR CAPSULES

BACKGROUND OF THE INVENTION

This invention relates to compressible starches suitable for use as binders in tablets or capsules. It also relates to a method for preparing and characterizing suitable compressible starches. Tablets and capsules usually consist of or contain several inert materials, referred to as excipients, in addition to the active ingredient which is present in amounts sufficient to accomplish the desired pharmaceutical, nutritive, or chemical effect. These excipients are generally classified according to their functions, such as diluents (also called bulking agents and fillers), binders which hold the ingredients together, and binder-diluents which perform both functions. Tablets may also contain disintegrants which help the tablet to break apart and release the active ingredient when placed in a fluid environment, lubricants to improve the release of the compressed tablet from the die and punches, glidants to improve the flow, and anti-adhesives to prevent film formation on the punches. Other optional ingredients may be dyes, flavors, sweeteners, antioxidants and/or sorbents.

Tabletting and some capsule-filling operations are based on the ability of certain powders to bind under compression. Compressed tablets may be prepared by wet granulation, dry granulation (e.g., slugging), or direct compression [see pp. 318–323 of "The Theory and Practice of Industrial Pharmacy", L. Lachman, H. A. Lieberman, and J. L. Kanig (Eds.), Lea & Febiger, Philadelphia, PA 1970 for a discussion of these tabletting methods]. Common dry dosage capsule-filling operations make use of a material that can be gravity- or force-fed into the capsule or a material that can be formed into a plug which is then used to fill the capsule. For the former a material which improves the flow properties of the powder mix is desirable. For the latter a binder-diluent which is easily compressed under low pressure to form a soft plug is required.

Briefly, the steps involved in a typical wet granulation include mixing the components, preparing the granulating binder solution, thoroughly mixing the components with the granulating binder solution to form a dough, coarse screening the moist mass through a sieve, drying, grinding, adding the lubricant, and compressing the tablets.

The steps involved in slugging are mixing the powdered components, compressing the mixture into hard slugs, grinding the slugs to the desired particle size, screening, adding the other excipients, and compressing the mixture into tablets.

The most preferred and economical tabletting method, direct compression, requires only two steps- mixing the dry components and compressing the mixture into tablets.

The binders or binder-diluents used in the above tabletting or capsule-filling operations should be stable, non-reactive and non-hygroscopic, free-flowing powders with some compressibility. The binders used for direct compression tabletting require excellent binding properties.

Typical wet granulation binders include starch pastes, conventional pregelatinized starches, gelatin, polyvinylpyrrolidone, methyl cellulose, sucrose, dextrose, and natural gums. The use of conventional starch binders, such as a pregelatinized, modified and stabilized waxy maize starch, pregelatinized corn starch, pregelatinized tapioca starch, stable modified amylopectin, low viscosity tapioca dextrin, dextrinized corn starch and/or cold-water-swelling pregelatinized corn starch, in Vitamin C tablets is disclosed in U.S. Pat. No. 3,453,368 issued July 1, 1969 to L. Magid. These starches which are water-soluble do not have direct compression properties and can not be used in direct compression tabletting.

Typical direct compression binders include microcrystalline cellulose, compressible sugars, specific calcium salts, lactose, and dextrose. Of these, microcrystalline cellulose seems to be the best binder and it also displays good disintegration properties. However, tablets made with this binder tend to have dull rough surfaces. Also microcrystalline cellulose is very expensive. Other good binders include the calcium phosphates (di- or tribasic) and compressible sugars, but each has its disadvantage. Namely, the calcium salts do not allow one to prepare tablets with a high level of active ingredient and generally require the use of disintegrants. The sugars (mostly made up of sucrose) present a darkening problem, tend to increase in hardness with age, and possibly react with drugs. Lactose has limited binding properties and exhibits a browning reaction when exposed to heat and moisture; it also requires the use of a disintegrant. Mannitol and sorbitol have certain taste advantages but either lack binding properties and require a disintegrant or are too hygroscopic or too expensive.

Starch as a binder should not be confused with starch as a disintegrant or diluent since different properties are required for each use. The most important property required in a binder is compressibility. Granular starches and conventional pregelatinized (i.e. cooked, non-granular, cold-water-dispersible starches) do not bind well under direct compression.

Physically modified, partially cold-water-swelling, cold-water-soluble compacted starches are reportedly useful as binder-disintegrants for direct compression tabletting (see U.S. Pat. Nos. 3,622,677 and 4,072,535 issued Nov. 23, 1971 and Feb. 7, 1978 to R. W. P. Short et al.) and as free-flowing fillers for dry dosage capsules (see U.S. Pat. No. 4,072,535 cited above). The modification, which is carried out by passing the starch through closely spaced steel rollers with or without the use of supplemental thermal energy, disrupts and fractures at least some of the granules and results in a mixture of birefringent and non-birefringent granules and fragments, as well as completely solubilized starch (typically about 10–20%). The compacted mass is ground and classified into particle size fractions. The resulting starch does have limited direct compression binding but the loading potential is low and the use of an auxiliary binder is often required.

Physically modified starches, which are cold-water-swellable but limited in their cold-water solubility (i.e., less than 10% by weight), are useful as disintegrants for various tabletting methods (see U.S. Pat. No. 4,383,111 issued May 10, 1983 to K. Takeo et al.) but not as binders. The processed starch is prepared by adding water and optionally an organic solvent to a grain starch (e.g., corn, wheat, or rice) to form a dispersion having a solids content of not more than 30% by weight, heating the dispersion at a temperature higher than 50° C. but not exceeding 10° C. higher than the gelatinization temperature of the native starch therein, and drying the dispersion without destruction of the shell film structure. The starch granule is swollen without destruction of the shell film structure and rendered non-birefringent.

Chemically modified starches, such as starch derivatives and crosslinked pregelatinized starches, are useful as disintegrants but not as binders. The derivatives, e.g., starch phosphate, starch sulfate, and carboxymethyl starch, which are cold-water-swelling, cold-water-soluble intact granular starches, are described in U.S. Pat. No. 3,034,911 issued May 15, 1962 to I. K. McKee et al. The low swelling, crosslinked and pregelatinized starches, which are characterized by their uniformly swollen, virtually non-birefringent granules, are described in U.S. Pat. No. 4,369,308 issued Jan. 18, 1983 to P. C. Trubiano.

Hydrolyzed starches, such as dextrinized starches having a DE of from about 0.5–50, are used as "melting point elevators" in a hybrid wet granulation-direct compression tabletting process for preparing nonfriable, rapidly water-soluble tablets such as sweetened or unsweetened beverage tablets (see U.S. Pat. No. 4,384,005 issued May 17, 1983 to D. R. McSweeney). An aqueous moistener comprising corn syrup and optionally glycerine is added to the dry mix containing the acidulant and optional components, and the hydrolyzed starch is added in an amount sufficient to function as a melting point elevator and also to convert the moistened mixture into a free-flowing mixture suitable for direct compression. The melting point elevator raises the melting point of the mixture so that the tablet will not soften, melt or form a hard core during the optional drying step that follows tablet formation.

Starch fractions, such as non-granular amylose, are also reportedly useful as binder-disintegrants in direct compression or double compression (dry slugging) tabletting processes (see U.S. Pat. No. 3,490,742 issued Jan. 20, 1970 to G. K. Nichols et al.) but are not suitable as wet granulation binders. The amylose fraction is non-granular because the starch from which it is derived is totally solubilized in order to free the amylose. This material is prepared by fractionating starch and then gelatinizing the fractionated amylose or by dissolving granular high amylose starch in water at elevated temperatures whereby it is gelatinized. In these processes the granular structure is destroyed.

There is, therefore, a need for non-chemically-modified, multifunctional compressible starches which are suitable for use as binders in any tabletting method, especially direct compression, and which are likewise useful as binder-diluents for capsule filling operations.

SUMMARY OF THE INVENTION

In one embodiment, the present invention provides a compressible starch, useful as a binder for tablets prepared by direct compression or dry granulation or as a binder-diluent for capsules, which consists essentially of a free-flowing compressible starch powder derived from a cold-water-insoluble, granular starch base by treatment with an acid, alkali, and/or alpha amylase enzyme at a temperature below the gelatinization temperature of the starch, the treated starch being characterized by altered, weakened granules with a less dense interior and disrupted surface, the starch powder effectively binding when compressed. The compressible starch may be admixed with other excipients and still provide an acceptably compressible mixture which results in hard tablets (i.e., a hardness of at least 5 kg.). The methods used for preparing the compressible starches are described hereafter.

In another embodiment, it provides a starch-containing admixture, useful as a binder for tablets prepared by direct compression, dry granulation or wet granulation or as a binder-diluent for capsules, which is an admixture of the above compressible starch and an effective amount of a wet granulation binder, e.g., pregelatinized starch. The admixture is prepared by dry blending about 15–85%, preferably 40–85%, most preferably 75%, of the compressible starch powder with about 15–85%, preferably 15–50%, most preferably 25%, of the wet granulation binder, the percentages being by weight and totaling 100%.

The more highly treated the starch is, the more compressible it is, provided some or most of the granular structure is retained. If the treatment is carried out at a temperature above the individual starch's gelatinization temperature, a non-compressible starch will be formed because the granular structure will be destroyed.

The treatment alters the region within the starch granule which consists of closely packed crystalline and amorphous regions. It is believed that primarily the amorphous regions are attacked and weakened, as by erosion. This causes the formation of voids or low density areas leaving behind the crystalline portion of the granule. The treatment also affects the surface morphology of the granule. The figures described hereafter show the alterations caused by the treatment. Acid-treatment generally roughens the surface of the granule as the outer layers are visually eroded; the remains of this erosion process can be seen as flakes on the surface. Enzyme-treatment with alpha-amylase leads to the formation of pits, craters or crevices, and in extreme cases holes or fissures which penetrate the entire granule. Acid/enzyme-treated starches show both the roughened surface and pits, craters or the like. It is believed that, when the treated starch is compressed, there is a repositioning or deformation of many parts of the granule.

Oxidation (e.g., with sodium hypochlorite) and extensive derivatization (e.g., with propylene oxide) of the granule also provide compressible properties. These treatments, however, bring about actual chemical changes in the starch molecule. Treatment with an oxidizing agent converts a limited number of hydroxy groups to aldehyde, ketone, and carboxyl groups, whereas treatment with a derivatizing reagent introduces ether or ester substituent groups. Such chemical changes may cause an interaction with the active ingredients and are not desirable for pharmaceutical applications.

The treated starches herein are particularly useful as binders for pharmaceutical tablets requiring superior binding properties. They are stable, non-hygroscopic, and non-reactive and have excellent direct compression binding properties as well as good disintegration properties.

BRIEF DESCRIPTION OF THE DRAWINGS

For a more complete understanding of the nature and scope of the alterations in the starch granule, reference may be made to the accompanying drawings wherein:

FIG. 1 is a scanning electron microphotograph of unmodified waxy corn starch granules which shows the smooth, unaltered granular surface.

FIG. 2 is a microphotograph corresponding to an enlarged individual granule of FIG. 1.

FIGS. 3 and 4 are microphotographs of compressible acid-treated waxy maize starch granules, useful herein, which show the roughened granular surface and fragments or flakes on the outer layer of the granule.

FIG. 5 is a microphotograph of compressible enzyme-treated waxy maize starch granules, prepared under relatively mild treatment conditions and useful herein, which shows the formation of pits in the granular surface.

FIG. 6 is a microphotograph of compressible enzyme-treated waxy maize starch granules, prepared under much stronger treatment conditions and useful herein, which shows further erosion of the granular surface and the deeper craters formed therein.

FIG. 7 is a microphotograph of compressible acid-/enzyme-treated waxy maize starch granules, useful herein, which shows both the roughened surface characteristic of the acid treatment and the pits and craters characteristic of the enzyme treatment.

FIG. 8 is a microphotograph of an unmodified potato starch granule which shows the smooth unaltered granular surface.

FIG. 9 is a microphotograph of a compressible acid-/enzyme-treated potato starch granule, useful herein, which shows the roughened granular surface.

FIG. 10 is a microphotograph of a group of compressible acid/enzyme-treated potato starch granules, useful herein, which shows the varied altered granular surfaces (roughened and/or pitted surface and eroded interior).

FIG. 11 is a microphotograph of an individual granule of FIG. 10 which shows the eroded interior of a granule.

FIG. 12 is a microphotograph of an unmodified tapioca starch granule.

FIG. 13 is a microphotograph of a compressible acid-treated tapioca starch granule, useful herein, which shows the altered granular surface.

The above microphotographs were taken using a scanning electron microscope at 25 KV. FIGS. 1, 3, 5–9, and 11–13 were taken at a magnification of 2000×, FIGS. 2 and 4 at a magnification of 5000×, and FIG. 10 at a magnification of 300×. The acid, enzyme, and acid/enzyme treatment conditions resulting in the above altered starch granules are described in the following examples. Corn starch granules show the same changes as the waxy corn starch granules shown in FIGS. 1–7.

DESCRIPTION OF THE PREFERRED EMBODIMENTS

The applicable starch bases which may be used in preparing the acid and/or enzyme-treated starches may be derived from any plant source. These include starches such as corn, potato, sweet potato, wheat, rice, sago, tapioca, sorghum, high amylose starches, and the like. Corn starch and waxy corn starch are preferred as it is easier to alter their granular structure compared to other starches such as potato which have a more highly organized structure and hence are more resistant to the treatment. Hybridized waxy corn starches such as those disclosed in U.S. Pat. No. 4,428,972 issued January 31, 1984 to O. B. Wurzburg et al. are less suitable since they can not withstand the temperatures used in most treatments, but treatment can be adapted.

The enzymes used to treat most of the starches herein are alpha amylases from a bacterial source such as those sold under the trade names BAN 120L and Thermamyl 60L by Novo Co. Equally compressible starches can be made using an alpha amylase from a fungal source such as that sold under the trade name Fungamyl 800L by Novo Co.

The acid-treated starches are prepared by conventional procedures well-known to those skilled in the art and described in such articles as "Starch and Its Modifications" by M. W. Rutenburg, Chapter 22 in Handbook of Water-Soluble Gums and Resins, R. L. Davidson (Ed.), McGraw Hill Book Co. (New York) 1980. These starches, often referred to as fluidity starches, are prepared by hydrolyzing the starch base in the presence of an inorganic or organic acid, preferably mineral acids such as sulfuric or hydrochloric acid, at a temperature below the gelatinization point of the starch. The starch is slurried in water, and the acid is then added. The treatment is carried out for a time sufficient to provide a minimum water fluidity (W.F.) of 60. Typically, the reaction takes place over a 8–16 hr. period, after which the acid is neutralized with alkali (e.g. to a pH of 5.5), and the starch recovered by filtration and dried at a temperature below the gelatinization temperature to its natural moisture content. The resulting starch will require grinding to provide the free-flowing starch powder useful as the compressible binder.

The enzyme-treated starches are prepared by a procedure which is significantly different from a conventional enzyme treatment. It is carried out on a granular starch base using moderately high amounts of enzyme (e.g., 0.1–1.0%) at a temperature below the starch's gelatinization temperature (e.g., about 55° C. for a long period of time (e.g., 1→12 hr.). A conventional enzyme treatment is carried out on a gelatinized starch base using a low level enzyme (e.g., 0.02%) at a temperature above the starch's gelatinization temperature (e.g., >70° C.) for a relatively short time (e.g., about 15–30 min.). The enzyme-treated granular starch herein can be recovered by filtration or centrifugation, whereas a conventional enzyme-treated starch must be recovered by spray-or freeze-drying, drum-drying, alcohol precipitation, and the like.

Typically, they are prepared by slurrying the starch base in water, adjusting the pH to 5.0–6.5 with alkali or acid, adding an effective amount of alpha amylase enzyme (e.g., about 0.1–1% on the starch), and then heating at a temperature below the gelatinization point of the starch. The treatment is carried out for a time sufficient to produce at least about 3.5% reducing sugars (R.S.) which is related to a Brabender viscosity reduction as described hereafter. The pH is lowered to about 2.0 with acid to deactivate the enzyme and that pH is maintained for a period of at least 10 minutes. Thereafter the pH may be readjusted upward. The resulting starch will likewise require drying as any normal granular starch and grinding prior to use as a binder.

Suitable starches may also be prepared by treatment with alkali (see Starch Chemistry and Technology, Roy L. Whistler and Eugene F. Paschall (Eds.), Vol. I, Chapter XXI for a discussion of the alkaline treatment of starch). Typically, the granular starch is suspended in water and treated with 1.2% sodium hydroxide (on the weight of starch) for 24 hours at a temperature below the starch's gelatinization temperature. The treatment is carried out in a closed oxygen-free system to prevent oxidation. The alkali is neutralized with dilute hydrochloric acid and the starch is filtered, washed, and dried. The resulting compressible starches are also useful herein, but more difficult to recover.

In the preparation of the compressible starches herein, the amount of treatment required to render the granule compressible will vary with the starch base and the amount of granular alteration desired. The treatment should be sufficient to alter the granule as monitored by the production of reducing sugars for the enzyme-treated starches, reduction in water fluidity for the acid-treated starches, and water fluidity or production of reducing sugars for the acid/enzyme-treated starch or enzyme/acid-treated starch. These alterations are evidenced by changes in the granular interior and surface when viewed under the scanning electron microscope.

The reducing sugars produced during the enzyme-treatment are removed during the washing step. For the enzyme-treatment the production thereof is correlated to a reduction in the Brabender viscosity of the enzyme-treated starch base over that of the untreated starch base. The reduction is at least about 35% from the peak or final viscosity, whichever reduction is greater.

Corn and waxy corn starches prepared by acid treatment should have a water fluidity of at least 60. Corn and waxy corn starches prepared by enzyme treatment should produce at least about 3.5% R.S. This results in a reduction in final viscosity of about 35% for corn and a reduction in peak viscosity of about 35% for waxy corn. Starches of 80 W.F. or above or the production of about 14–18% R.S. (resulting in a Brabender viscosity reduction of about 45% or greater) are preferred. The treated corn and waxy corn starches prepared by the dual treatment, i.e. acid/enzyme-treated or enzyme/acid-treated, should show the same water fluidity or production of reducing sugars. For example, if the starch is acid-treated to a WF of 60 or above, the production of reducing sugars is not necessary. If the starch is acid-treated to a WF of <60, the subsequent enzyme-treatment must produce at least about 3.5% R.S. The converse is true for the enzyme/acid-treated starches. If the enzyme-treatment produces at least about 3.5% R.S., the water fluidity does not have to be >60 and if it produces <3.5% R.S., the water fluidity must be >60.

It is within the skill of the practitioner to determine suitable treatment levels for other starch bases using the guidelines provided herein, i.e., granular alteration as evidenced by the production of reducing sugars, and/or water fluidity or Brabender viscosity reduction, by the compressibility of the treated starch, and in the scanning electron microphotographs. The relative ease with which starches from various sources are treated varies from easy to difficult and the amount of reducing sugars necessary to prepare a compressible starch will also vary. The guideline of at least 3.5% reducing sugars will apply to most starches; however, with potato starch it is necessary to produce about 8% reducing sugars to obtain a compressible starch.

The treated starches are pulverized to a particle size compatible with the particle size of the other tabletting components. Preferably, the starch is pulverized to a particle size such that at least 98% passes through a 40 mesh screen (0.0425 cm.–0.0165 in.). The mesh number refers to a U.S. standard sieve. A very fine particle size is not always desirable. Some very finely pulverized binders, when used with coarse tabletting components, may initially form a homogeneous mixture but will subsequently stratify, thus giving a non-homogeneous mixture. This is the case with all tablet excipients. Typically, the pulverization step is carried out in a hammer mill such as Raymond, Fitzmill, or MikroPulverizer.

The wet granulation binders useful in the binder admixture are conventional, well-known and discussed previously. Pregelatinized starches such as corn starch are preferred herein.

The active ingredients which may be employed herein constitute all active ingredients and include pharmaceutical active ingredients. The particular nature of the active ingredient is not critical, however, and non-pharmaceutical active ingredients such as pulverized detergents, dyes, pesticides, and foods may also be employed.

In addition to good binding properties, the compressible starch binders herein, as well as their admixtures with the wet granulation binders, show good disintegration properties in most cases without the use of additional disintegrants. When necessary, disintegrants may be used and these include native starches, modified starches, gums, cellulose derivatives, microcrystalline cellulose, clays, effervescent mixtures, and enzymes.

The amount of binder (or binder admixture), active ingredient, and lubricant, disintegrant and/or diluent, if any, will depend not only on potency desired but also on the compatibility of the components, the tabletting method used, and also the hardness, friability, disintegrability, dissolution, and/or stability of the final tablet. The amount of binder-diluent used in the dry dosage capsules will likewise depend on various factors. Given the minimum and preferred characteristics desired in the final product, the tolerable limits on the weight ratio of the components may be easily determined by the skilled practitioner. Anti-adhesives, glidants, flavors, coloring agents, and the like may also be used. They are incorporated in appropriately effective amounts into the tablets herein.

The following examples will more fully illustrate the embodiments of this invention. In the examples, all parts are given by weight and are based on the weight of the starch, and all temperatures are in degrees Celsius.

The following procedures were used to characterize the compressible starch powders useful herein, to monitor their preparation, and to prepare and evaluate tablets containing these compressible starches as binders.

Reducing Sugars

The production of reducing sugars is determined by the Eynon-Lane Volumetric Method using Fehling's solution as described in the Cane Sugar Handbook by Spencer and Meade, John Wiley and Sons, Inc., 8th Edition at p. 412 and 423. The test sugar solution is prepared by washing the granular enzyme-treated starch mixture sufficiently to remove all sugar from the starch. The filtrate is collected and brought to a known concentration. This sugar solution is used to reduce a known amount of the Fehling's solution.

Water Fluidity

Water fluidity of the starches is measured using a Thomas Rotational Shear-Type Viscometer (manufactured by Arthur H. Thomas Co., Philadelphia, PA 19106), standardized at 30° C. with a standard oil having a viscosity of 24.73 cps., which oil requires 23.12 ±0.05 sec. for 100 revolutions. Accurate and reproducible measurements of the water fluidity are obtained by determining the time which elapses for 100 revolutions at different solids levels depending on the starch's degree of treatment (as treatment increases, the viscosity decreases). The procedure used involves slurrying the required amount of starch (e.g., 11.44 or 13.20 g. dry basis) in 100 ml. of distilled water in a covered copper cup and heating the slurry in a boiling water bath for 30 min. with occasional stirring. The starch dispersion is then brought to the final weight (e.g., 113 or 115 g.) with distilled water. The time required for 100 revolutions of the resultant dispersion at 81°–83° C. is recorded and treated to a water fluidity number as defined in the table below.

| Amount of Starch Used (anhydrous): | | |
|---|---|---|
| 11.44 g.* Time required for 100 revolutions (sec.) | 13.20 g.** | Water Fluidity |
| 32.5 | | 45 |
| 26.8 | | 50 |
| 22.0 | | 55 |
| | 24.2 | 60 |
| | 19.2 | 65 |
| | 15.9 | 70 |
| | 13.5 | 75 |
| | 11.5 | 80 |
| | 10.0 | 85 |
| | 9.0 | 90 |

* and ** Final weight of starch solutions are 113 and 115 g., respectively.

Brabender Viscosity Breakdown

The starch to be tested is slurried in a sufficient amount of distilled water to give 460 g. slurry containing sufficient anhydrous starch to give a slurry containing 6% solids for waxy corn starch or 7% solids for corn starch. The slurry is poured into the Brabender cup, and the viscosity in Brabender units (B.U.) is measured using a VISCO/Amylo/GRAPH (manufactured by C. W. Brabender Instruments, Inc., Hackensack, N.J.). The slurry is brought to 30° C. and is heated to 95° C. at a heating rate of 1.5° C. per minute and held at 95° C. for 15 minutes. The peak and final viscosity readings were recorded. A 350 cm.-g. cartridge is used for all the viscosity readings.

The percent loss in viscosity is based on either peak viscosity or final viscosity (95° C.+15 min.), whichever shows a greater difference from the base starch. This will depend upon the starch source.

% Loss in Viscosity =

$$\frac{(\text{Base Viscosity} - \text{Treated Viscosity})}{\text{Base Viscosity}} \times 100$$

Tablet Preparation and Evaluation

All of the tablets were made using a Stokes B-2, 16 station rotary tablet press equipped with 0.95 cm. (⅜ in.) standard concave punches. Tablet weight was determined by averaging the readings of ten tablets weighed on an appropriate balance. A Delamar PT-1000 hydraulic tablet hardness tester was used to determine tablet strength by averaging the readings of ten tablets. The starches used as binders, including the compressible starches, pregelatinized starch used as a wet granulation binder, and comparative starches used in the following examples, all had a comparable particle size.

EXAMPLE I

This example shows how the degree of acid treatment, as indicated by water fluidity, affects the compressibility of starch granules as indicated by tablet hardness at the optimum compression setting which corresponds to a pressure of about 176 kg./cm² (2500 lb./in.²).

The starch was suspended in water at 40% solids (as is). Concentrated hydrochloric acid was added and the slurry was heated to 52° C. and maintained at that temperature for the indicated time. The mixture was then neutralized with alkali to a pH of about 6, filtered, washed, dried, and ground in a Hammer Mill to a particle size of 98% through 40 mesh.

The results are shown in Tables I & II.

TABLE I

| Starch Base | Designation | Treatment Conditions | | Viscosity (W.F.) | Tablet Hardness (kg.) |
|---|---|---|---|---|---|
| | | HCl (%) | Time (hr.) | | |
| Corn | Control | — | — | — | 2.0 |
| Corn | A | 0.7 | 8 | 40 | 2.0 |
| Corn | B | 0.9 | 8 | 61 | 6.0 |
| Corn | C | 7.0 | 19 | 85 | 8.7 |
| Corn | D | 7.0 | 22 | 86 | 10.1 |
| Corn | E | 7.0 | 26 | 87 | 10.3 |
| Corn | F | 12.0 | 50 | >90 | 11.0 |

TABLE II

| Starch Base | Designation | Treatment Conditions | | Viscosity (W.F.) | Tablet Hardness (kg.) |
|---|---|---|---|---|---|
| | | HCl (%) | Time (hr.) | | |
| Waxy Corn | Control | — | — | — | 2.5 |
| Waxy Corn | G | 0.6 | 8 | 29 | 1.5 |
| Waxy Corn | H | 0.7 | 8 | 50 | 2.3 |
| Waxy Corn | I | 1.8 | 8 | 74 | 8.1 |
| Waxy Corn | J | 3.1 | 8 | 82 | 8.9 |
| Waxy Corn | K | 10.0 | 24 | >90 | 10.4 |
| Waxy Corn | L | 10.0 | 50 | >90* | 15.0 |
| Waxy Corn | M | 50.0 | 90 | >90* | >20.0 |

*Significantly greater than 90.

The results show that tablet hardness is related to the amount of treatment, with more extensively treated starches producing stronger harder tablets. A hardness of 5 kg. is the minimal acceptable value since weaker tablets will easily break apart when handled. Starches having a W.F. of about 60 or higher are sufficiently altered to be compressible, whereas untreated starches and lightly treated starches, which also show no significant granular alterations, are not suitable binders.

FIGS. 3 and 4 show a compressible waxy maize starch prepared by acid treatment with 3.1% acid for 8 hours (starch designated J - in Table 1). The treatment has caused erosion of the granular surface. Granules of the most highly treated waxy corn starch, M (not shown), were observed to be weak skeletons with the amorphous regions totally dissolved away. Acid-treated compressible corn starch (not shown) exhibits similar changes on the granular surface.

EXAMPLE II

This example shows how the enzyme treatment, as indicated by the viscosity loss and reducing sugars, produced affects the compressibility of starch granules.

The starch was suspended in water at about 40% solids (as is). Calcium chloride at 0.25% on the weight of the starch was added to help stabilize the enzyme. The pH of the slurry was adjusted to 6.0–6.5. The bacterial alpha-amylase enzyme (Ban 120L described previously) was added and the temperature was increased to 55° C. The pH was maintained at 6.0–6.5 by the addition of dilute alkali. After the indicated reaction time, the enzyme was deactivated by dropping the pH to about 2-3 with dilute acid and then held for at least 10 minutes before the pH was adjusted to about 6 with alkali. The starch was washed, dried, and then ground as before. The enzyme amount and reaction time are given in Tables III-IV, which also include data on the amount of reducing sugar produced, Brabender viscosity reduction, and tablet hardness.

TABLE III

| Starch | | Treatment Conditions | | | Viscosity | | Tablet Hardness (kg.) |
|---|---|---|---|---|---|---|---|
| Base | Designation | Enzyme (%) | Time (hr.) | R.S. (%) | Peak (B.U.) | Loss (%) | |
| Waxy Corn | Control | — | — | <0.9 | 1800 | — | 3.0 |
| Waxy Corn | A | 1.0 | 0.5 | 2.4 | 1220 | 32 | 3.8 |
| Waxy Corn | B | 1.0 | 2.0 | 5.0 | 1090 | 39 | 5.9 |
| Waxy Corn | C | 1.0 | 4.0 | 6.3 | 955 | 47 | 6.3 |
| Waxy Corn | D | 1.0 | 16.5 | 11.9 | 835 | 54 | 9.5 |
| Waxy Corn | Comparative | — | 16.5 | <0.9 | 1665 | 7.5 | 3.0 |

The results in Table III show that waxy corn starch can be rendered compressible by enzyme treatment and that tablet hardness is related to the extent of treatment. Good binding properties are obtained when the percent loss in peak viscosity is about 35% or greater which corresponds to the production of about 2.4–5.0% reducing sugars. The level of reducing sugars reflects the degree to which the amorphous areas of the granule have been affected. The untreated starches were not suitable as binders nor were the comparative starches similarly treated but without enzyme.

TABLE IV

| Starch | | Treatment Conditions | | | Viscosity after Treatment | | Tablet Hardness (kg.) |
|---|---|---|---|---|---|---|---|
| Base | Designation | Enzyme (%) | Time (hr) | R.S. (%) | Final (B.U.) | Loss (%) | |
| Corn | Control | — | — | <0.9 | 860 | — | capped* |
| Corn | E | 1.0 | 1.0 | 3.2 | 550 | 36 | 4.8 |
| Corn | F | 1.0 | 4.0 | 6.1 | 510 | 41 | 5.4 |
| Corn | G | 1.0 | 16.5 | 11.2 | 530 | 38 | 7.3 |
| Corn | Comparative | — | 16.5 | <0.9 | 880 | (−2) | 4.0 |

*Could not be formed into a tablet.

The results in Table IV show that enzyme-treated corn starch is compressible and effective as a tablet binder. Due to the characteristics of corn starch the final viscosity rather than the peak viscosity was used to determine the viscosity reduction required to provide good binding. It is again shown that increasing treatment provides stronger tablets and that a loss in final viscosity of about >36% is required to provide an altered granule with sufficient compressiblity to give a tablet with a hardness of 5 kg. This treatment corresponds to the production of >3.2% R.S.

FIGS. 5 and 6 show waxy corn starch granules altered by enzyme treatment with about 1.0% enzyme for about 4.0 and 16.5 hours (starches designated C and D in Table III). The surface is pitted, with the more highly treated starch showing an increased number of pits and deeper pits. Compressible corn starch, not shown, exhibits similar pits.

EXAMPLE III

This example shows the use of combined acid/enzyme-treatments.

The starch was acid-treated as in Example I and, after neutralization of the acid with alkali, treated with the enzyme as in Example II. The conditions, water fluidity, reducing sugars, and tablet hardness are given in Table V.

TABLE V

| Starch | | Acid Treatment | | Viscosity (W.F.) | Enzyme Treatment | | | Viscosity (W.F.) | Tablet Hardness (kg.) |
|---|---|---|---|---|---|---|---|---|---|
| Base | Designation | HCl (%) | Time (hr.) | | Enzyme (%) | Time (hr.) | R.S. (%) | | |
| Waxy Corn | A | 3.1 | 8 | 76 | — | — | <0.5 | 76 | 6.0 |
| Waxy Corn | B | 3.1 | 8 | 76 | 1.0 | 7.5 | 10.8 | 77 | 7.9 |
| Waxy Corn | C | 3.1 | 8 | 76 | 1.0 | 10.0 | 11.5 | 77 | 12.3 |

The results show that the combination treatment provides a starch with increased binding properties. The compression results showed that the strength actually improved over that of the acid-treated starch base (7.9 and 12.3 vs. 6.0 kg). The enzyme further alters the granular structure to favor compressibility and the resultant binding properties, as observed by the increased production of reducing sugars (10.8 and 11.5% vs. <0.5% for the acid-treated base) even though the W.F. did not change significantly.

FIG. 7 shows waxy corn starch granules altered by acid/enzyme-treatment with 3.1% acid for 8 hr. and 1.0% enzyme for 7.5 hr. (starch designated B in Table V). The granules show the roughened surface typical of the acid treatment and pits typical of enzyme treatment. Corn starch granules similarly treated will show the same changes.

EXAMPLE IV

This example further studies the dual treatment to determine the required water fluidity or generation of reducing sugars for waxy corn starch.

Part A

An acid-treated starch having a WF of 50, which had been treated with 0.7% HCl for 12-14 hr. at 50°-52° C., was further treated with 1% alpha-amylase at 55° C. as indicated in Table VI.

TABLE VI

| Acid-Treated Starch Base (50 W.F.) | Enzyme Treatment | | Tablet Hardness (kg.) |
|---|---|---|---|
| | Time (hr.) | R.S (%) | |
| Waxy Corn | — | <0.9 | 2.5 |
| Waxy Corn | 0.25 | 2.1 | 4.0 |
| Waxy Corn | 0.5 | 3.2 | 4.8 |

TABLE VI-continued

| Acid-Treated Starch Base (50 W.F.) | Enzyme Treatment Time (hr.) | R.S (%) | Tablet Hardness (kg.) |
|---|---|---|---|
| Waxy Corn | 1.00 | 3.6 | 6.0 |

The results show that if the acid-treated starch base has a WF below 60, the level of reducing sugars necessary to provide satisfactory binding properties is still about 3.5% (same as for the enzyme-treated starch base.

Part B

An enzyme-treated corn, treated with 1% alpha-amylase for 0.5 hr. at 55° C. to produce 2.2% reducing sugars, was further treated at 52° C. for 16.5 hr. with acid as indicated in Table VII.

TABLE VII

| Enzyme-Treated Starch Base (2.2% R.S.) | Acid Treatment HCl (%) | Viscosity (W.F.) | Tablet Hardness (kg.) |
|---|---|---|---|
| Waxy Corn | — | <8 | 3.5 |
| Waxy Corn | 0.6 | 46 | 4.3 |
| Waxy Corn | 0.8 | 59 | 4.8 |
| Waxy Corn | 1.0 | 62 | 5.1 |
| Waxy Corn | 1.2 | 68 | 5.5 |

The results show that if the enzyme-treated starch base has produced less than about 3.5% reducing sugars, the water fluidity necessary to provide satisfactory binding properties is at least about 60 W.F. (the same as it is for the acid-treated starch base).

The treatment is thus independent of the sequence, but it must result in at least a 60 WF starch or in the production of at least about 3.5% reducing sugars.

EXAMPLE V

This example demonstrates that other starch bases can be used to produce compressible starches. The starch bases, treatment conditions, and tablet hardness are shown in Table VIII.

The results show that all starch bases could be acid and/or enzyme-treated to provide compressible starch granules. The level and type of treatment depended largely on the starch source, as well as interplay of crystalline and amorphous regions within the granule. When the granule was sufficiently altered, as shown in FIGS. 9, 10, 11 and 13, the starch was compressible with good binding properties. Waxy sorghum

TABLE VIII

| Starch Base | Acid Treatment HCl (%) | Time (hr.) | Temperature °C. | Viscosity (W.F.) | Enzyme Treatment Enzyme (%) | Time (hr.) | Temperature (°C.) | R.S. (%) | Tablet Hardness (kg.) |
|---|---|---|---|---|---|---|---|---|---|
| Potato (control) | — | — | — | — | — | — | — | — | N.M. |
| Potato | — | — | — | — | 2 | 44 | 40 | 3.7 | 1.0 |
| Potato | 10 | 18 | 52 | 88 | — | — | — | — | N.M. |
| Potato | 10 | 18 | 52 | 89 | 1 | 17 | 55 | 8.8 | 5.2 |
| Tapioca (control) | — | — | — | — | — | — | — | — | 3.0 |
| Tapioca | — | — | — | — | 1 | 18 | 55 | 10.2 | 4.0 |
| Tapioca | 11 | 18 | 52 | 90 | — | — | — | — | 10.0 |
| Tapioca | 11 | 18 | 52 | 85 | 1 | 16 | 55 | 12.5 | 11.4 |
| High Amylose* (control) | — | — | — | — | — | — | — | — | 4.0 |
| High Amylose | — | — | — | — | 1 | 18 | 55 | 10.1 | 4.0 |
| High Amylose | 10 | 18 | 52 | 88 | — | — | — | — | 7.5 |
| High Amylose | 10 | 18 | 52 | 88 | 1 | 17 | 55 | 10.5 | 7.0 |
| Rice (control) | — | — | — | — | — | — | — | — | 4.6 |
| Rice | — | — | — | — | 1 | 6 | 55 | 4.9 | 8.3 |
| Waxy Sorghum (control) | — | — | — | — | — | — | — | — | 3.0 |
| Waxy Sorghum | — | — | — | — | 1 | 17 | 55 | 13.6 | 15.8 |

*70% amylose.
N.M. - not made and rice starch needed only enzyme treatment to sufficiently alter their granular structure and provide binding properties. Enzyme treatment alone did not sufficiently alter tapioca or high amylose corn starch, but acid treatment or a dual acid/enzyme treatment provided sufficient change in the granule to give binding properties (see FIGS. 12 and 13 which show unmodified and altered tapioca granules). Potato starch was very resistant to the action of enzyme or acid, but acid treatment followed by enzyme treatment altered the granular structure sufficiently to render the starch compressible (see FIGS. 8–11 which show unmodified and altered potato starch granules). The acid treatment conditions the granule so that the enzyme can penetrate the granule more easily during the subsequent treatment.

EXAMPLE VI

This example demonstrates the good disintegration properties of the compressible starch binders and compares their performance with those of other conventional direct compression binders. All tests were done with 99.5% binder and 0.5% magnesium stearate as a lubricant. Tablet weights were held constant at 340±30 mg. unless otherwise noted, but the tablet hardness was varied.

Disintegration times were determined according to method <70> for uncoated tablets using water at 37°±2° C. as the medium (see U.S. Pharmacopeia National Formulary, USP XX, NF XV p. 958, 1980). The results are shown in Table VIII.

TABLE IX

| Binder | Description | Desintegration Rates (min.' sec.") at Hardness of: 4–7 kg. | 7–9.6 kg. |
|---|---|---|---|
| Acid-Treated Starch | Waxy Corn (89 W.F.) | 2'20" | 5'00" |
| Enzyme-Treated Starch | Waxy Corn (11.9% R.S. produced) | 1'10" | 2'05" |
| Acid/Enzyme-Treated Starch | Waxy Corn (86 W.F.) (14% R.S. produced) | 1'10" | 3'00" |
| Starch 1500 (comparative) | Precompacted corn starch from Colorcon Corp. | 15'00" | N.M. |
| Avicel PH 101 (comparative) | Microcrystalline cellulose from | 18" | 4'28" |

TABLE IX-continued

| Binder | Description | Desintegration Rates (min.' sec.") at Hardness of: | |
|---|---|---|---|
| | | 4-7 kg. | 7-9.6 kg. |
| Emdex (comparative) | FMC Corp. Compressible sugar from Mendell Co. | 2'38" | 4'00" |
| Emcompress (comparative) | Dicalcium Phosphate Dihydrate from Mendell Corp. | None* | None* |

*Weight was 575 ± 20 mg.
N.M. - tablets could not be made

The results show that the compressible starches herein disintegrated much faster than most of the conventional direct compression (D.C.) binders tested. They also show that most of the direct compression binders either have slow disintegration rates at low tablet strength, initially have excellent disintegration rates but become progressively poorer with increasing tablet hardness, or do not break up or swell in water.

Example VII

This example demonstrates the usefulness of the compressible starches in wet granulation. When combined with a wet granulation (W.G.) binder, the resulting admixture not only maintains the excellent direct compression properties shown in the preceding examples but also enhances the binding properties when such admixtures are used in wet granulation.

| Starch Ratio | | Hardness (kg.) | |
|---|---|---|---|
| Treated Starch | Pregelatinized Starch* | D.C.** | W.G.*** |
| 100 | 0 | 14.2 | did not granulate |
| 85 | 15 | 13.4 | 10.1 |
| 75 | 25 | 13.1 | 10.3 |
| 50 | 50 | 10.9 | N.D. |
| 25 | 75 | 7.4 | 10.4 |
| 20 | 80 | 6.5 | N.D. |
| 10 | 90 | 4.2 | N.D. |
| 0 | 100 | 3.4 | 10.3 |

*Drum-dried corn starch
**99.5 parts binder, 0.5 part magnesium stearate
***Vitamin C - 10 parts binder and 90 parts Vitamin C
N.D. - Not determined because no variation was noted.

The results show that the direct compression properties are maintained in the admixture and that there is a synergistic effect between the components when used in wet granulation. The above data shows that W.G. tablets of equal hardness are produced whether the wet granulation component (i.e., pregelatinized starch) is used at 100% or is extensively diluted with as much as 85% of the treated starch component (i.e., the compressible starch). The results also show that for D.C. tablets with acceptable hardness (5 kg. or greater) at least about 15%, preferably 25%, of the compressible starch should be present in the admixture.

EXAMPLE VIII

This example shows the use of the binder admixture to prepare tablets containing active ingredients using both tabletting methods. It also compares the resultant tablets with tablets prepared using other binders. The admixture comprised 75 parts of the waxy corn starch of Table IX (dual treatment) and 25 parts of pregelatinized (i.e., drum-dried) corn starch.

VITAMIN C TABLETS

D.C. tablets were prepared by dry blending 50.00 parts ascorbic acid, 49.0 parts binder, and 1.00 part stearic acid (triple pressed) and then tabletted.

W.G. tablets were prepared by dry blending 90 parts ascorbic acid and 10.00 parts binder, granulating with 12-13% water in a Hobart mixer using speed #1, precompacting the granulate by passing it through the grinder attachment of the Hobart, oven drying at 120° C. to <0.6% moisture, and grinding through a #20 sieve on #100 sieve. A total of 98.80 parts of the above ground dry granulate was dry blended with 1.00 part stearic acid (triple pressed), and 0.20 part magnesium stearate and tabletted.

ASPIRIN TABLETS

D.C. tablets were prepared by dry blending 59.0 parts acetaminophen, 0.55 part Cabosil EH-5 (amorphous fumed silica sold by Cabot Corp.) and 0.55 part Syloid-244 (silica gel sold by W. R. Grace Co.) and screening through a #20 sieve. A mixture of 38.30 parts binder, 1.05 steric acid (triple pressed), and 0.55 part magnesium stearate was added to the above mixture, screened through the #20 sieve, and tabletted.

W.G. tablets containing a starch disintegrant were prepared by dry blending 90 parts USP aspirin crystals and 10.0 parts binder, granulating and precompacting as above, and screening through a #10 sieve. The granulate was oven dried at 80° C. to <2.0% moisture, ground through a #16 sieve, and collected on a #40 sieve. A total of 96.00 parts of the dry screened granulate was then dry blended with 3.00 parts of a disintegrant, 0.70 part stearic acid (triple pressed) and 0.30 part magnesium stearate and tabletted.

Tablets were prepared by adjusting the weight and pressure settings of the tablet press to give the optimum strength with the bifunctional binder in each of the series below. The other binders of each set were then prepared at the same pressure setting but the weight was varied for the comparative study. The results are given below.

| Type | Method | Binder | Weight (mg.) | Hardness (kg.) | Disintegration Time (min.) |
|---|---|---|---|---|---|
| Vitamin C | D.C. | Acid/enzyme-treated waxy corn and drum-dried corn starches | 524 | 9.0 | 18 |
| | | | 523** | 5.2 | 8 |
| Vitamin C | D.C. | Starch 1500* | 521 | 5.3 | 15 |
| Vitamin C | D.C. | Hydrous Lactose* | 519 | 4.3 | 4 |
| Vitamin C | D.C. | Compressible Sugar* | 524 | 5.7 | 7 |
| Vitamin C | D.C. | Dicalcium Phosphate Dihydrate* | 522 | 3.6 | 26 |
| Aspirin | D.C. | Acid/enzyme-treated waxy corn and drum- | 477 | 8.4 | 1 |
| | | | 496** | 6.7 | 1 |

-continued

| Type | Method | Binder | Weight (mg.) | Hardness (kg.) | Disintegration Time (min.) |
|---|---|---|---|---|---|
| | | dried corn starches | | | |
| Aspirin | D.C. | Starch 1500* | 480 | 6.6 | 1 |
| Aspirin | D.C. | Hydrous Lactose* | 488 | 1–2 | 60 |
| Aspirin | D.C. | Compressible Sugar* | 484 | 1–2 | 60 |
| Aspirin | D.C. | Dicalcium Phosphate Dihydrate* | 477 | 1–2 | >60 |
| Vitamin C | W.G. | Acid/enzyme-treated waxy corn and drum-dried corn starches | 520 | 11.1 | 28 |
| Vitamin C | W.G. | Starch 1500* | 523 | 10.4 | 41 |
| Vitamin C | W.G. | Drum-dried corn* | 524 | 11.3 | 47 |
| Aspirin | W.G. | Acid/enzyme-treated waxy corn and drum-dried corn starches | 365 | 8.6 | 23.5 |
| Aspirin | W.G. | Starch 1500* | 364 | 7.4 | 21 |
| Aspirin | W.G. | Drum-dried corn* | 374 | 7.8 | 22 |

*Comparative
**Tabletted at lower pressure settings to obtain reduced hardness.

The results show that the binder admixture formed harder D.C. tablets than the other binders at the same pressure and that the disintegration times were in most cases better. The results show that the bifunctional binder can be used satisfactorily in the W.G. tablets and is at least comparable to or better than the other starch binders.

EXAMPLE IX

This example demonstrates that the compressible starch herein and its admixture with pregelatinized starch would be useful as binder-diluents in dry capsule filling operations.

Depending on the capsule filling equipment, a binder-diluent which improves the flow properties of the powder mix is desired to assure even distribution during the filling step. In other cases, a soft plug is made to fill the capsule and a material which easily compresses under low pressure to form a soft plug is required.

Both the compressible starch and its admixture were free-flowing by themselves and improved the flow properties when mixed with active ingredients such as Vitamin C. Further, they formed soft, cake-like masses easily when the powder was squeezed between the thumb and forefinger unlike native starches and pregelatinized starches. This suggests that the compressible starches and their admixtures with pregelatinized starches, when used in a capsule-filling machine, would form soft plugs which could be transferred intact to the capsule.

Summarizing, this invention is seen to provide unique multifunctional, free-flowing, readily compressible starches which are useful alone or in admixture with wet granulation binders, especially pregelatinized starches, as binders in any tabletting method or as binder-diluents in dry capsule filling operations.

Now that the preferred embodiments of the present invention have been described in detail, various modifications and improvements thereto will become readily apparent to those skilled in the art. Accordingly, the spirit and scope of the invention are to be limited only by the appended claime and foregoing specification.

What is claimed is:

1. A starch, useful as a binder for tablets prepared by direct compression or dry granulation or as a binder-diluent for capsules, which consists essentially of a free-flowing, compressible starch powder derived from a cold-water-insoluble, granular starch base by treatment with an acid, and/or alpha-amylase enzyme, the treatment of the starch base and recovery of the free-flowing, compressible starch powder being carried out at a temperature below the gelatinization temperature of the starch; the treated starch being characterized by altered, weakened non-gelatinized granules with a less dense interior and disrupted surface; the compressible starch powder being capable of forming, under direct compression, a tablet having a hardness of at least 5 kg.

2. The binder of claim 1, wherein the compressible starch powder is an acid and/or enzyme-treated corn, waxy corn, high amylose corn, potato, tapioca, rice, wheat, or waxy sorghum starch.

3. The binder of claim 2, wherein the compressible starch powder is an acid/enzyme-treated corn or waxy corn starch.

4. The binder of claim 2, wherein the acid-treated starch is a corn or waxy corn starch having a water fluidity of at least 60 WF, wherein the enzyme-treated starch is a corn or waxy corn starch which produces at least about 3.5% reducing sugars during the treatment, and wherein the acid/enzyme-treated starch or enzyme/acid-treated starch is a corn or waxy corn starch which has a water fluidity of at least 60 or produces at least about 3.5% reducing sugars during the treatment.

5. The binder of claim 4, wherein the production of at least about 3.5% reducing sugars in the enzyme treatment relates to a Brabender viscosity reduction of at least about 35% under the peak or final Brabender viscosity of the non-treated granular starch base, whichever reduction is greater.

6. The binder of claim 5, wherein the acid-treated starch has a water fluidity of about 80 or above, wherein the enzyme-treated starch has a Brabender viscosity about 45% less than that of the non-treated granular corn or waxy corn starch, and wherein the acid/enzyme-treated starch has a water fluidity of at least 80 or produces at least about 14% reducing sugars during the treatment.

7. The binder of claim 6, wherein the treated corn starch has a reduction in final viscosity and the treated waxy corn starch has a reduction in peak viscosity.

8. A starch-containing admixture, suitable as a binder for tablets prepared by direct compression, dry granulation, or wet granulation or as a binder-diluent for capsules, which consists essentially of an admixture of a compressible starch powder and an effective amount of a wet granulation binder; the compressible starch being an acid-, and/or alpha-amylase enzyme-treated starch powder derived from a cold-water-insoluble, granular starch base by treatment of the starch base and recovery of the free-flowing, compressible starch powder at a temperature below the gelatinization temperature of the starch, the compressible starch powder being characterized by altered, weakened non-gelatinized granules with a less dense interior and disrupted surface; the admixture effectively binding when compressed.

9. The admixture of claim 8, wherein the compressible starch powder is an acid and/or enzyme-treated corn, waxy corn, high amylose corn, potato, tapioca, rice, wheat, or waxy sorghum starch and wherein the wet granulation binder is a pregelatinized starch.

10. The admixture of claim 10, wherein the compressible starch is a corn or waxy corn starch and the pregelatinized starch is corn starch.

11. The admixture of claim 10, wherein the compressible starch is present in an amount of about 40–85% and the pregelatinized starch is present in an amount of about 15–60%.

12. The admixture of claim 11, wherein the compressible starch is present in an amount of about 75% and the pregelatinized starch is present in an amount of about 25%.

13. The admixture of claim 12, wherein the acid-treated starch has a water fluidity of at least 60, wherein the enzyme-treated starch produces at least about 3.5% reducing sugars during the treatment, and wherein acid-/enzyme-treated or enzyme/acid-treated starch has a water fluidity of at least 60 or produces at least about 3.5% reducing sugars during the treatment.

14. The admixture of claim 13, wherein the production of at least about 3.5% reducing sugars in the enzyme treatment relates to a Brabender viscosity reduction of at least about 35% under the peak or final Brabender viscosity of the nontreated granular starch base, whichever reduction is greater.

15. The admixture of claim 14, wherein the acid-converted starch has a water fluidity of about 80 or above, wherein the enzyme-treated starch has a Brabender viscosity about 45% less than that of the non-treated granular starch, and wherein the acid/enzyme-treated starch has a water fluidity of at least 80 or produces at least about 14% reducing sugars during the treatment.

16. The admixture of claim 15, wherein the enzyme-treated corn starch has a reduction in final Brabender viscosity and the treated waxy corn has a reduction in peak viscosity.

17. The non-friable, hard tablet prepared by direct compression or dry granulation, which comprises a tabletting mixture of an active ingredient and an effective amount of the compressible starch binder of claim 1.

18. The capsule, which comprises plugs of a dry capsule mixture of an active ingredient and an effective amount of the compressible starch binder of claim 1.

19. The non-friable, hard tablet prepared by direct compression or dry or wet granulation, which comprises a tabletting mixture of an active ingredient and an effective amount of the admixture of claim 8.

20. The capsule, which comprises plugs of a dry capsule mixture of an active ingredient and an effective amount of the admixture of claim 8.

* * * * *

REEXAMINATION CERTIFICATE (604th)
United States Patent [19]
Trubiano et al.

[11] B1 4,551,177

[45] Certificate Issued Dec. 23, 1986

[54] COMPRESSIBLE STARCHES AS BINDERS FOR TABLETS OR CAPSULES

[75] Inventors: Paolo C. Trubiano; James J. Kasica, both of Somerville, N.J.

[73] Assignee: National Starch and Chemical Corporation, Bridgewater, N.J.

Reexamination Request:
No. 90/000,987, Apr. 14, 1986

Reexamination Certificate for:
Patent No.: 4,551,177
Issued: Nov. 5, 1985
Appl. No.: 603,021
Filed: Apr. 23, 1984

[51] Int. Cl.$^4$ .................. C08B 31/00; C08L 3/00
[52] U.S. Cl. .................................. 106/210; 106/213; 127/32; 127/71; 536/102
[58] Field of Search .................. 106/210; 127/32

[56] References Cited
U.S. PATENT DOCUMENTS
4,383,111  5/1983  Takeo et al. .................. 536/102

FOREIGN PATENT DOCUMENTS
51-28700 of 1976 Japan.

OTHER PUBLICATIONS
"Organic Chemistry", Morrison et al., 1973, p. 526.

*Primary Examiner*—Theodore Morris

[57] ABSTRACT

A compressible starch, useful as a binder for tablets prepared by direct compression or dry granulation or as a binder-diluent for capsules, is prepared by treating a cold-water-insoluble, granular starch (e.g., corn or waxy corn starch) with an acid, and/or alpha-amylase enzyme at a temperature below the starch's gelatinization temperature. The treated starch is characterized by altered, weakened granules with a less dense interior and disrupted surface. The compressible starch when admixed with a wet granulation binder (e.g., pregelatinized starch) is useful as a binder for tablets prepared by wet granulation as well as direct compression or dry granulation or as a binder-diluent for capsules.

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 5-17, 19 and 20 is confirmed.

Claims 1-4 and 18 are cancelled.

* * * * *